US010549033B2

(12) United States Patent
Shimizu

(10) Patent No.: US 10,549,033 B2
(45) Date of Patent: Feb. 4, 2020

(54) INFUSION PUMP

(71) Applicant: TERUMO KABUSHIKI KAISHA, Tokyo (JP)

(72) Inventor: Nobutaka Shimizu, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 315 days.

(21) Appl. No.: 14/664,259

(22) Filed: Mar. 20, 2015

(65) Prior Publication Data

US 2015/0238689 A1    Aug. 27, 2015

Related U.S. Application Data

(63) Continuation of application No. PCT/JP2012/006217, filed on Sep. 27, 2012.

(51) Int. Cl.
*A61M 5/172* (2006.01)
*A61M 5/142* (2006.01)

(52) U.S. Cl.
CPC .......... *A61M 5/172* (2013.01); *A61M 5/1422* (2013.01); *A61M 5/14276* (2013.01)

(58) Field of Classification Search
CPC ................ A61M 5/172; A61M 5/1422; A61M 5/14228; A61M 5/14276;
(Continued)

(56) References Cited

U.S. PATENT DOCUMENTS 5,336,884 A * 8/1994 Khoshnevisan ..... G01D 5/2497
                                              250/231.14
5,419,684 A     5/1995 Struble et al.
(Continued)

FOREIGN PATENT DOCUMENTS

CN    102022308    4/2011
EP     0560270     9/1993
(Continued)

OTHER PUBLICATIONS

2011/0230712; U.S. Pat. No. 8,216,128, Sep. 22, 2011, Matsuura et al.
(Continued)

*Primary Examiner* — Kevin C Sirmons
*Assistant Examiner* — Leah J Swanson
(74) *Attorney, Agent, or Firm* — Jason H. Vick; Sheridan Ross, PC

(57) ABSTRACT

[Problem] Provided is an infusion pump in which a forward rotation and a reverse rotation of a rotor of a drive motor can be detected so as to be able to safely deliver drug to a patient. An infusion pump 1 includes a drive motor 61, a liquid delivering drive unit 60 that delivers drug inside an infusion tube by Dressing an infusion tube 200 on account of a rotor of the drive motor 61 in forward rotation, a rotational direction detection device 700 that generates detection information 780 regarding a rotational direction for judging whether the rotor of the drive motor 61 is in the forward rotation or reverse rotation, and a control unit 100 that judges whether a rotor 161A of the drive motor 61 is in the forward rotation or the reverse rotation based on the detection information 780 regarding the rotational direction obtained from the rotational direction detection device 700.

20 Claims, 7 Drawing Sheets

(58) Field of Classification Search
CPC .. A61M 2005/16863; A61M 2205/106; G01D 5/249; G01D 5/2451; G01D 5/2454; G01D 5/2455; G01D 5/2457; G01D 5/2458; G01D 5/2497; G01D 5/347; G01D 5/3473

See application file for complete search history.

(56) References Cited

U.S. PATENT DOCUMENTS

| | | | | |
|---|---|---|---|---|
| 5,522,799 | A * | 6/1996 | Furukawa | A61M 5/142 128/DIG. 12 |
| 6,078,273 | A * | 6/2000 | Hutchins | G01D 5/2451 318/640 |
| 2002/0143290 | A1 * | 10/2002 | Bui | A61M 5/172 604/67 |
| 2003/0028145 | A1 * | 2/2003 | Duchon | A61B 6/481 604/151 |
| 2003/0205587 | A1 | 11/2003 | Tribe et al. | |
| 2011/0060284 | A1 | 3/2011 | Harr | |
| 2012/0078222 | A1 | 3/2012 | Smith et al. | |
| 2012/0235674 | A1 * | 9/2012 | O'Gorman | G01D 5/145 324/207.25 |

FOREIGN PATENT DOCUMENTS

| | | |
|---|---|---|
| JP | S64-28517 | 1/1989 |
| JP | H11-500338 | 1/1999 |
| JP | 2001-520905 | 11/2001 |
| JP | 3267404 | 3/2002 |
| JP | 2002-113099 | 4/2002 |
| JP | 2006-271769 | 10/2006 |
| JP | 2011/194155 | 10/2011 |
| WO | WO 97/007843 | 3/1997 |
| WO | WO 99/21481 | 5/1999 |
| WO | WO 99/021481 | 7/1999 |
| WO | WO 2012/120765 | 9/2012 |

OTHER PUBLICATIONS

Extended European Search Report for European Patent Application No. 12885538.4, dated Apr. 18, 2016, 13 pages.

International Search Report for International Patent Application No. PCT/JP2012/006217, dated Jan. 8, 2013, 4 pages.

Li, et al., "A Method for Quickly Testing Rotation Direction of Motors," Journal of Shandong Institute of Eng., 1996, vol. 10(2), 3 pages.

Extended European Search Report for European Patent Application No. 17207218.3, dated Mar. 14, 2018, 12 pages.

Written Opinion for International Application No, PCT/JP2012/006217, dated Jan. 8, 2013.

International Preliminary Report on Patentability for International Application No. PCT/JP2012/006217, dated Apr. 9, 2015.

* cited by examiner

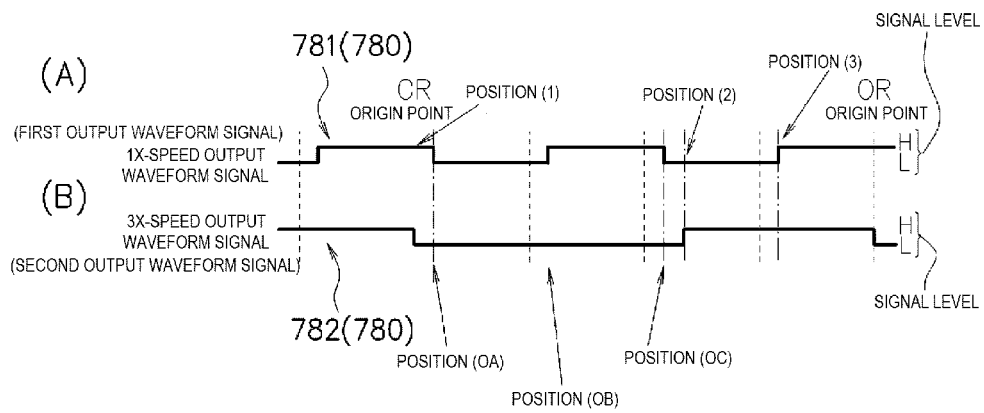

FIG. 7

| | | CURRENT ENCODER INFORMATION IF1 | | | |
|---|---|---|---|---|---|
| | (781) (782) 1X SPEED; 3X SPEED | L:L (1-1) | L:H (1-2) | H:L (1-3) | H:H (1-4) |
| IMMEDIATE-LY PRECEDING ENCODER INFORMA-TION IF0 | L:L (2-1) | NO POSITIONAL CHANGE | FORWARD ROTATION: POSITION (2) | FORWARD ROTATION: POSITION (OB), REVERSE ROTATION: POSITIONS (OA, OC) | ROTATION: POSITION UNIDENTIFIED |
| | L:H (2-2) | REVERSE ROTATION: POSITION (2) | NO POSITIONAL CHANGE | ROTATION: POSITION UNIDENTIFIED | FORWARD ROTATION: POSITION (3) |
| | H:L (2-3) | FORWARD ROTATION: POSITIONS (OA, OC), REVERSE ROTATION: POSITION (OB) | ROTATION: POSITION UNIDENTIFIED | NO POSITIONAL CHANGE | REVERSE ROTATION: POSITION (1) |
| | H:H (2-4) | ROTATION: POSITION UNIDENTIFIED | REVERSE ROTATION: POSITION (3) | FORWARD ROTATION: POSITION (1) | NO POSITIONAL CHANGE |

FIG. 8

INFUSION PUMP

CROSS REFERENCE TO RELATED APPLICATIONS

This Application is a continuation of and claims priority to PCT/JP2012/006217, filed Sep. 27, 2012, entitled "Infusion Pump," which is incorporated herein by reference in its entirety for all that it teaches and for all purposes.

TECHNICAL FIELD

The present invention relates to an infusion pump for delivering drug to a patient.

BACKGROUND ART

An infusion pump is used in an intensive care unit (ICU) or the like, for example, and is adopted to perform delivering treatment of drug for a patient at relatively high accuracy for a relatively long period of time. A prejudged drug bag (an infusion bag) is arranged on the top of the infusion pump and an infusion tube suspended from the drug bag is interposed between a main body and an opening/closing door. The infusion tube is accommodated in the main body and is held therein by closing the opening/closing door. In the main body of the infusion pump, an outer circumferential surface of the infusion tube set in a home position is interposed between a plurality of fingers inside the main body and an inner surface of the opening/closing door. The infusion pump is a peristaltic infusion pump in which a drive motor operates to deliver drug by causing the plurality of fingers to sequentially press the outer circumferential surface of the infusion tube along a longitudinal direction (refer to PTL 1).

CITATION LIST

Patent Literature

PTL 1: Japanese Patent No. 3267404

DISCLOSURE OF INVENTION

Technical Problem

In an infusion pump of the related art, detection has been performed in a rotor of a drive motor regarding only a forward rotation. When there is an occurrence of an occlusion in an infusion tube, the rotor of the drive motor needs to be reversely rotated as mitigation treatment for the occlusion. However, no infusion pump has been proposed which detects quantity of reverse rotation of the rotor of the drive motor.

The present invention aims to provide an infusion pump in which a forward rotation and the reverse rotation of the rotor of the drive motor can be detected together with a rotational speed thereof so as to be able to safely deliver drug to a patient.

Solution to Problem

According to an aspect of the present invention, there is provided an infusion pump for delivering drug to a patient by causing a distal opening portion of an endovascular indwelling catheter or an indwelling needle which communicates with an infusion tube to indwell inside a vein or an intestinal tract of the patient. The infusion pump includes a drive motor, a liquid delivering drive unit that delivers the drug inside the infusion tube by pressing the infusion tube on account of a rotor of the drive motor in forward rotation, a rotational direction detection device that generates detection information regarding a rotational direction for judging whether the rotor of the drive motor is in the forward rotation or reverse rotation, and a control unit. The control unit judges whether the rotor of the drive motor is in the forward rotation or the reverse rotation based on the detection information regarding the rotational direction obtained from the rotational direction detection device. The control unit also judges whether or not a rotational speed of the rotor is normal.

According to another aspect of the present invention, there is provided an infusion pump for delivering drug to a patient by causing a distal opening portion of an endovascular indwelling catheter or an indwelling needle which communicates with an infusion tube to indwell inside a vein or an intestinal tract of the patient. The infusion pump includes a drive motor, a liquid delivering drive unit that delivers the drug inside the infusion tube by pressing the infusion tube on account of a rotor of the drive motor in forward rotation, a rotational direction detection device that generates detection information regarding a rotational direction for judging whether the rotor of the drive motor is in the forward rotation or reverse rotation, a downstream occlusion sensor that detects whether or not the infusion tube is occluded, and a control unit. The control unit judges whether the rotor of the drive motor is in the forward rotation or the reverse rotation based on the detection information regarding the rotational direction obtained from the rotational direction detection device. The control unit also judges whether or not a rotational speed of the rotor is normal. While causing the rotational direction detection device to detect that the rotor of the drive motor is in the forward rotation, if an occlusion state is detected by the downstream occlusion sensor when delivering liquid in the forward rotation, the control unit stops the forward rotation. While causing the rotational direction detection device to detect that the rotor of the drive motor is in the reverse rotation, the control unit controls the drive motor so as to be driven in the reverse rotation until fulfilling a prejudged condition.

According to the configuration described above, the control unit can judge whether the rotor of the drive motor is in the forward rotation or the reverse rotation based on the detection information regarding the rotational direction obtained from the rotational direction detection device. Therefore, it is possible to detect the forward rotation and the reverse rotation of the rotor of the drive motor so as to be able to safely deliver drug to a patient.

At the time of occlusion, it is possible to perform controlling for processing mitigation treatment of an occlusion pressure by causing the rotor to reversely rotate until a prejudged condition is fulfilled.

Preferably, the rotational direction detection device includes an encoder plate which is fixed to the rotor of the drive motor, and an optical coupler which obtains a first output waveform signal and a second output waveform signal different from the first output waveform signal by irradiating the encoder plate with light so as to send the first output waveform signal and the second output waveform signal to the control unit as the one-time detection information regarding the rotational direction.

According to the configuration described above, it is simply performed that the optical coupler optically generates the first output waveform signal and the second output waveform signal so as to send to the control unit as the detection information regarding the rotational direction of the rotor. Thus, it is possible to simplify the structure thereof.

Preferably, the first output waveform signal is an output waveform signal generated from the inner circumferential region of the light-blocking pattern and the second output waveform signal is an output waveform signal generated from the outer circumferential region of the light-blocking pattern. The control unit judges whether the rotor is in the forward rotation or the reverse rotation by comparing the first output waveform signal and the second output waveform signal.

According to the configuration described above, since the control unit has only to compare the first output waveform signal and the second output waveform signal, it is possible to accurately judge whether the rotor is in the forward rotation or the reverse rotation.

Preferably, the liquid delivering drive unit includes a plurality of cams which rotate on account of the forward rotation of the drive motor, and a plurality of fingers which deliver the drug inside the infusion tube while sequentially pressing the infusion tube in a longitudinal direction on account of the plurality of cams in rotation.

According to the configuration described above, the plurality of fingers can reliably deliver drug inside the infusion tube to a patient side by causing the plurality of cams to rotate forward.

Preferably, a display unit displaying information and an operation panel portion having an operation button are arranged in an upper portion of a main body of the infusion pump, and the infusion tube is arranged in a region of a lower portion of the main body of the infusion pump.

According to the configuration described above, a health care worker can perform delivering of drug by using the infusion pump while confirming the information on the display unit in the upper portion of the main body. Then, the health care worker can operate the operation button of the operation panel portion while confirming the information on the display unit in the upper portion of the main body.

Advantageous Effects of Invention

According to the present invention, it is possible to provide an infusion pump in which a forward rotation and a reverse rotation of a rotor of a drive motor can be detected so as to be able to safely deliver drug to a patient.

BRIEF DESCRIPTION OF DRAWINGS

FIG. 7 is a diagram illustrating an example of detection information regarding the rotational direction which can be obtained from an encoder plate.

FIG. 8 is a diagram illustrating an example of a judgment table for judging whether a magnet rotor and the output shaft of the drive motor illustrated in FIG. 6(A) are in rotation in a forward rotation direction CW or in rotation in a reverse rotation direction CCW, based on the detection information regarding the rotational direction illustrated in FIG. 7.

DESCRIPTION OF EMBODIMENTS

Hereinafter, a preferable embodiment of the present invention will be described in detail with reference to the drawings.

Since the below-described embodiment is a preferable specification example of the present invention, the embodiment is applied with various types of limitation which are technically preferable. However, the scope of the present invention is not limited to the aspects thereof unless there is disclosure particularly limiting the present invention in the following description.

Figure 1:
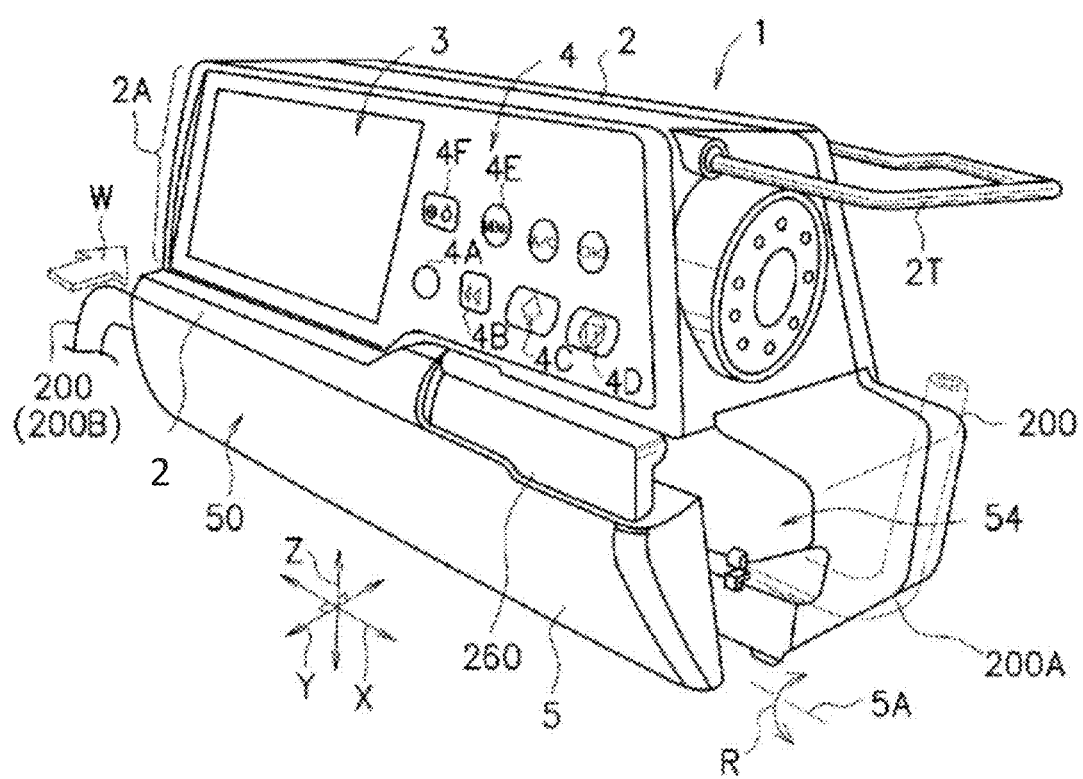
FIG. 1 is a perspective view illustrating a preferable embodiment of an infusion pump of the present invention.
Figure 2:
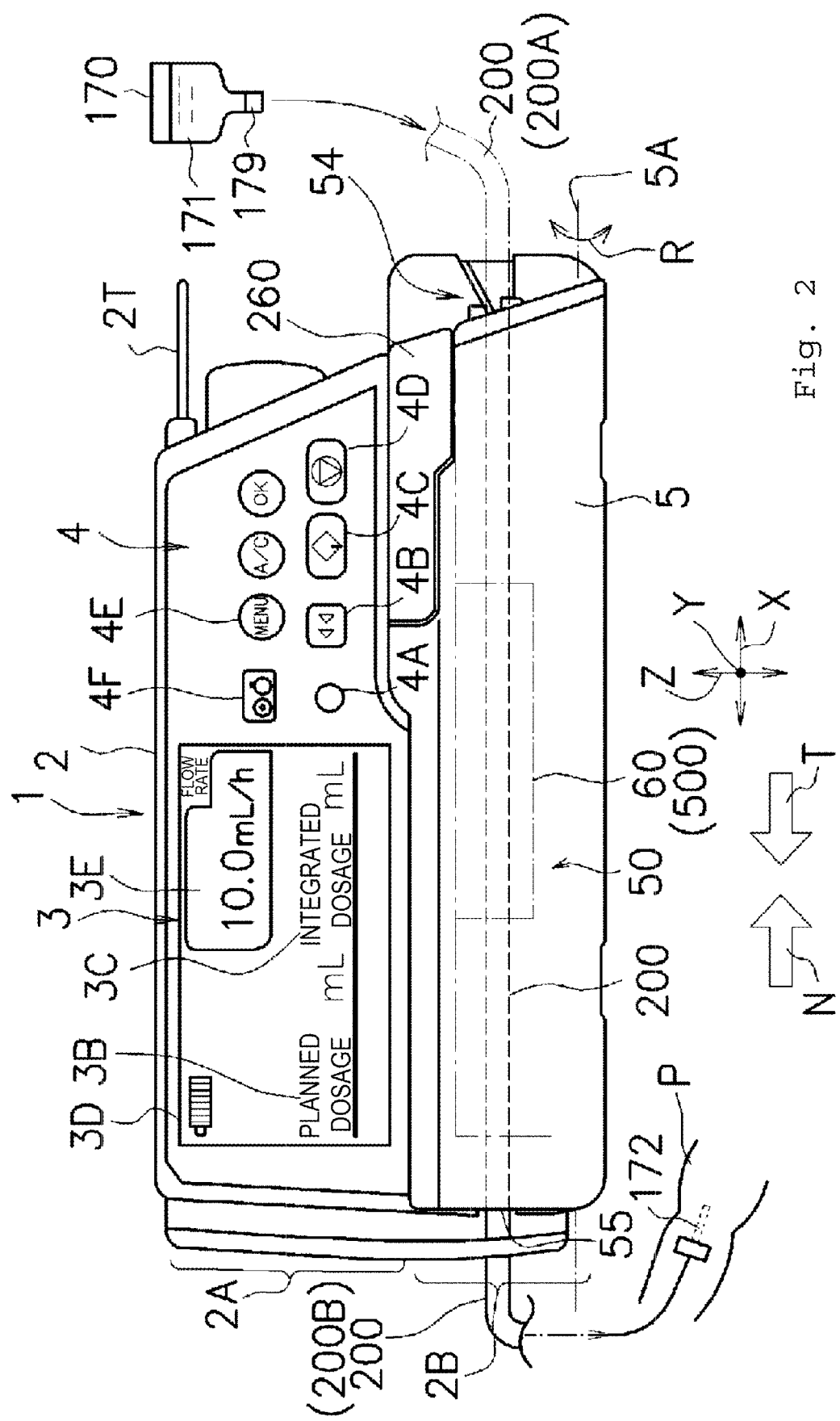
FIG. 2 is a diagram of the infusion pump illustrated in FIG. 1 when seen in a W-direction.

FIG. 1 is a perspective view illustrating an infusion pump which is the preferable embodiment of the infusion pump of the present invention. FIG. 2 is a diagram of the infusion pump illustrated in FIG. 1 when seen in a W-direction.

The infusion pump 1 illustrated in FIGS. 1 and 2 is a continuous infusion pump which is used for a patient in infusion treatment of drug (also referred to as a drug solution) such as an anticancer drug, an anesthetic, a chemotherapeutic and the like, infusion treatment of a nutrient, a blood transfusion and the like in intensive care units (ICU, CCU, NICU) or the like, for example, at relatively high accuracy for a relatively long period of time.

The infusion pump 1, for example, is used to select drug to be used from a drug library and to deliver the selected drug. The drug library is drug information of a dosage setting group of drug including the previously registered drug names in a drug library database (DB). A health care worker can select drug and can set the drug without performing complicated dosage setting every time by adopting the drug library.

As illustrated in FIG. 2, the infusion pump 1 can accurately deliver liquid to the inside of a patient P from a drug bag 170 filled with drug (or blood) 171 through a clamp 179, an infusion tube 200, and an indwelling needle or an endovascular indwelling catheter 172 caused to indwell inside a vein of the patient P. Drug is also referred to as an infusion solution. An infusion tube is also referred to as an infusion line.

Otherwise, the infusion pump 1 can accurately deliver liquid to the inside of the patient P from the bag 170 filled with a nutrient 171 through the clamp 179, the infusion tube 200, and a catheter 172 for indwelling inside an intestinal tract.

The infusion pump 1 has a main body cover 2 and a handle 2T. The handle 2T can be stretched in an N-direction and can be accommodated in a T-direction. The main body cover 2 is also referred to as a main body and is integrally molded with a molding resin material which is chemically resistant. The main body cover 2 has a drip-proof treated structure which can prevent the inside of the infusion pump 1 from being penetrated by drug even if the drug or the like is splashed over the main body cover. The main body cover 2 has such a drip-proof treated structure because there may be a case where the drug 171 in the drug bag 170 arranged in an upper portion is spilt, or an antiseptic solution or the like used in the vicinity thereof is splashed and adheres thereto.

Firstly, components arranged in the main body cover 2 of the infusion pump 1 will be described.

As illustrated in FIGS. 1 and 2, a display unit 3 and an operation panel portion 4 are arranged in an upper portion 2A of the main body cover 2. The display unit 3 is an image display apparatus, and a color liquid crystal display apparatus is used, for example. The display unit 3 can display information not only by notation in Japanese but also by notation in multiple foreign languages as necessary. The display unit 3 is arranged at an upper left position in the upper portion 2A of the main body cover 2, that is, on an upper side of an opening/closing cover 5. The upper portion 2A of the main body cover 2 is the upper half portion of the main body cover 2. The lower portion 2B of the main body cover 2 is the lower half portion of the main body cover 2.

In the upper portion 2A of the main body cover 2 of the infusion pump 1, the display unit 3 for displaying information and the operation panel portion 4 including a plurality of operation buttons are arranged. The lower portion 2B of the main body cover 2 of the infusion pump 1 is a region in which the infusion tube 200, that is, a delivery member for delivering drug is arranged. Accordingly, a health care worker can perform delivering of drug by using the infusion pump 1 while confirming information on the display unit 3 in the upper portion 2A of the main body cover 2. Then, the health care worker can operate the operation buttons of the operation panel portion 4 while confirming the information on the display unit 3 in the upper portion 2A of the main body cover 2. Therefore, the infusion pump 1 has favorable operability.

In FIG. 2, as an example, the display unit 3 displays a display section 3B for a planned dosage (mL) of drug, a display section 3C for an integrated dosage (mL) of drug, a display section 3D for a charge history, a display section 3E for a flow rate (mL/h) and the like. However, in the display unit 3 illustrated in FIG. 1, the aforementioned display contents are omitted in order to simplify the drawing. The display unit 3 can additionally display a warning message.

The operation panel portion 4 is arranged on the right side of the display unit 3 in the upper portion 2A of the main body cover 2. As the operation buttons in the illustrated example, a lamp 4A (formed with an LED, blinking or being lit in green during a normal operation, and blinking or being lit in red during an abnormal operation) which functions as an operational indicator, a fast-delivering switch button 4B, a start switch button 4C, a stop switch button 4D, a menu selection button 4E, a power switch 4F and the like are arranged in the operation panel portion 4, for example.

As illustrated in FIG. 1, the opening/closing cover 5 as a lid member is provided in the lower portion 2B of the main body cover 2 so as to be able to be in open and closed states in an R-direction having a rotary shaft 5A as the center. The opening/closing cover 5 is a plate-like lid member formed to be elongated along the X-direction. A tube mounting portion 50 and a liquid delivering drive unit 60 are arranged inside the opening/closing cover 5. The infusion tube 200 made of a flexible thermoplastic resin, soft vinyl chloride or the like, for example, is set to the tube mounting portion 50. As the opening/closing cover 5 is in the closed state, the infusion tube 200 can be horizontally mounted in the tube mounting portion 50 along an X-direction (the T-direction).

The X-direction, a Y-direction, and a Z-direction in FIGS. 1 and 2 are orthogonal to each other. The Z-direction is a vertical direction. The X-direction is a transverse direction of the infusion pump 1 parallel to the T-direction which is a delivering direction. The Y-direction is a front-rear direction of the infusion pump 1.

Figure 3:
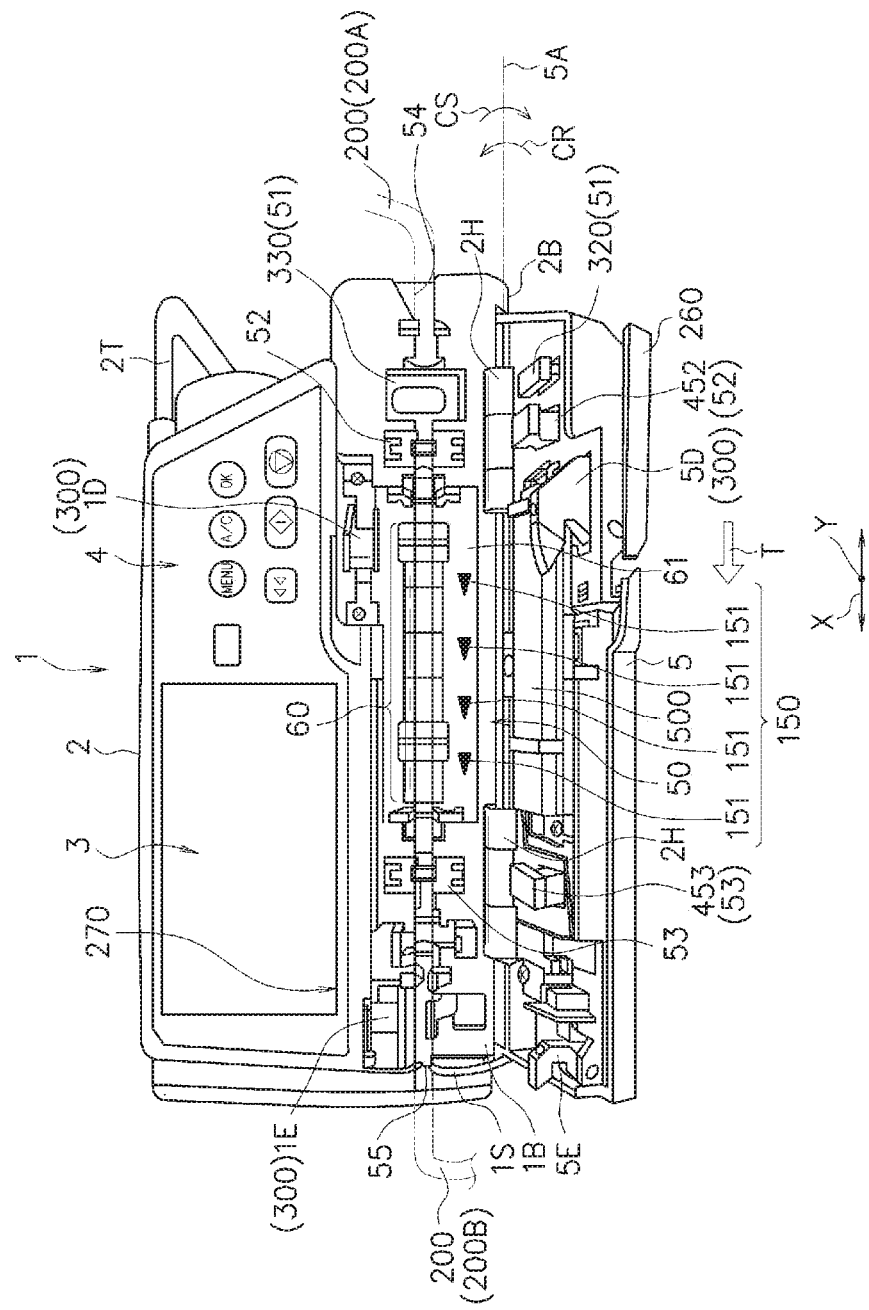
FIG. 3 is a perspective view illustrating an opening/closing cover of the infusion pump in an open state.

FIG. 3 is a perspective view illustrating the tube mounting portion 50 for mounting the infusion tube 200 by causing the opening/closing cover 5 of the infusion pump 1 illustrated in FIGS. 1 and 2 to be in an open state.

As illustrated in FIG. 3, the tube mounting portion 50 and the liquid delivering drive unit 60 are provided on a main body lower portion 1B side of the infusion pump 1. The tube mounting portion 50 and the liquid delivering drive unit 60 are provided along the X-direction at a lower portion of the display unit 3 and the operation panel portion 4. As illustrated in FIG. 2, the tube mounting portion 50 can be covered with the opening/closing cover 5 by closing the opening/closing cover 5 in a CR-direction having the rotary shaft 5A as the center.

A health care worker can mount the infusion tube 200 in the tube mounting portion 50 and close the opening/closing cover 5 while confirming the information on the display unit 3 in the upper portion 2A of the main body cover 2. Then, the health care worker can operate the operation buttons of the operation panel portion 4 while confirming the information on the display unit 3 in the upper portion 2A of the main body cover 2. Accordingly, in medical sites, operability of the infusion pump 1 can be improved.

As illustrated in FIG. 3, the tube mounting portion 50 includes an air bubble sensor 51, an upstream occlusion sensor 52, a downstream occlusion sensor 53, a tube clamp portion 270, a first infusion tube guide portion 54 at a position on the right side, and a second infusion tube guide portion 55 at a position on the left side.

As illustrated in FIG. 3, in the vicinity of the tube mounting portion 50, there is provided an infusion tube setting direction display portion 150 for clearly displaying the T-direction as the proper delivering direction when setting the infusion tube 200. For example, the infusion tube setting direction display portion 150 is configured to include a plurality of arrows 151. For example, the infusion tube setting direction display portion 150 may be directly printed on the lower portion of the tube mounting portion 50 or may be printed on a sticker-like member so as to be pasted on the lower portion of the tube mounting portion 50. The infusion tube setting direction display portion 150 is arranged in order to clarify the delivering direction (the T-direction) as the proper direction for the drug 171 which is delivered through the infusion tube 200 set inside the opening/closing cover 5.

Accordingly, it is possible to clarify the T-direction as the delivering direction of drug delivered through the infusion tube 200 when a health care worker undoes the opening/closing cover 5 of FIG. 3 in a CS-direction, opens the tube mounting portion 50, and causes the infusion tube 200 to be mounted in the tube mounting portion 50. Therefore, it is possible for a health care worker to be reliably prevented from erroneously mounting the infusion tube 200 in the reverse direction.

Subsequently, a structural example of the opening/closing cover 5 illustrated in FIG. 3 will be described.

As illustrated in FIG. 3, the opening/closing cover 5 is a plate-like member made with a thin molding resin member in order to achieve weight reduction of the infusion pump 1. In this manner, the weight of the opening/closing cover 5 can be reduced, and thus, the structure thereof can be simplified. The opening/closing cover 5 is supported by two hinge portions 2H and 2H with respect to the main body lower portion 2B of the main body cover 2 so as to be able to be in open and closed states and to cover the tube mounting portion 50 along the CS-direction and the CR-direction having the rotary shaft 5A as the center. The two hinge portions 2H and 2H are arranged so as to respectively correspond to a first hook member 5D and a second hook member 5E.

As illustrated in FIGS. 2 and 3, an opening/closing operation lever 260 is provided on an upper right portion of the opening/closing cover 5 on an outer surface side. An infusion tube pressing member 500, the first hook member 5D, and the second hook member 5E are provided inside the opening/closing cover 5. The infusion tube pressing member 500 is arranged as a protruding portion having an elongated rectangular and planar shape along the X-direction. The infusion tube pressing member 500 is at a position facing the liquid delivering drive unit 60. The infusion tube pressing member 500 has a flat surface in the X-direction along the liquid delivering drive unit 60. A portion of the infusion tube 200 is pressedly interposed between the infusion tube pressing member 500 and the liquid delivering drive unit 60 when the opening/closing cover 5 is in the closed state in the CR-direction.

A health care worker can set the infusion tube 200 in the lower half portion of the main body of the infusion pump 1 along a horizontal direction while confirming display contents displayed on the display unit 3. After the infusion tube 200 is set in the tube mounting portion 50, the opening/closing cover 5 can cover the infusion tube 200.

As illustrated in FIG. 3, the first hook member 5D and the second hook member 5E are respectively and mechanically interlocked with fixing portions 1D and 1E on the main body lower portion 1B side at the same time. Thus, as illustrated in FIG. 2, the opening/closing cover 5 maintains the tube mounting portion 50 at the main body lower portion 1B in a shut-down state. The first hook member 5D and the second hook member 5E including the fixing portions 1D and 1E on the main body lower portion 1B side are configured to form a double-hook structure portion 300 of the opening/closing cover 5.

The tube clamp portion 270 illustrated in FIG. 3 clamps an intermediate portion of the infusion tube 200 so as to be occluded by causing the opening/closing cover 5 to be in the closed state. The tube clamp portion 270 is arranged in the vicinity of the fixing portion 1E on the left side, that is, at a position corresponding to the second hook member 5E on the left side. As a health care worker sets the infusion tube 200 horizontally in the X-direction and the health care worker causes the opening/closing cover 5 to be in the closed state in the CR-direction, the tube clamp portion 270 can cause an intermediate portion of the infusion tube 200 to be occluded.

As illustrated in FIG. 3, the first infusion tube guide portion 54 is provided at a portion on the right to the main body lower portion 1B, and the second infusion tube guide portion 55 is provided at a portion on the left to the main body lower portion 1B. An upstream side 200A of the infusion tube 200 fits the first infusion tube guide portion 54 so as to be able to be held, and a downstream side 200B of the infusion tube 200 fits the second infusion tube guide portion 55 so as to be able to be held. Thus, the infusion tube 200 is held in the horizontal direction along the X-direction. In this manner, the infusion tube 200 held in the horizontal direction is fixed by being fit along the air bubble sensor 51, the upstream occlusion sensor 52, the liquid delivering drive unit 60, the downstream occlusion sensor 53, and the tube clamp portion 270 in the T-direction.

As illustrated in FIG. 3, the second infusion tube guide portion 55 is a groove portion formed in a side surface portion 1S of the main body lower portion 1B, thereby holding a portion of the downstream side 200B of the infusion tube 200 in a detachably interposed manner. Accordingly, the first infusion tube guide portion 54 and the second infusion tube guide portion 55 can be reliably mounted in the tube mounting portion 50 without nipping and squashing the infusion tube 200 between the opening/closing cover 5 and the tube mounting portion 50.

The air bubble sensor 51 illustrated in FIG. 3 is a sensor which detects air bubbles (air) generated in the infusion tube 200. For example, the air bubble sensor 51 is an ultrasonic sensor which monitors air bubbles included in drug flowing inside of the infusion tube 200 from outside the infusion tube 200 formed of soft vinyl chloride. Since transmittance of an ultrasonic wave of drug and transmittance of an ultrasonic wave of air bubbles are different from each other, an ultrasonic wave receiving unit detects the difference therebetween to monitor whether or not air bubbles are present by irradiating drug flowing inside of the infusion tube 200 with an ultrasonic wave generated from an ultrasonic wave oscillation unit of the ultrasonic sensor. The air bubble sensor 51 has a pressing member 320 and a receiving member 330. The ultrasonic wave oscillation unit is arranged in the pressing member 320. The ultrasonic wave receiving unit is arranged in the receiving member 330.

The upstream occlusion sensor 52 illustrated in FIG. 3 is configured to include a Hall element and a plunger. The upstream occlusion sensor 52 is a sensor which detects whether or not the inside of the infusion tube 200 is occluded on the upstream side 200A of the infusion tube 200 depending on whether or not degree ($\Delta$) of swelling (diameter expansion) of an outer diameter of the infusion tube 200 reaches a threshold value by detecting and outputting the swelling thereof. The downstream occlusion sensor 53 is configured to include the Hall element and the plunger. The downstream occlusion sensor 53 is a sensor which detects whether or not the inside of the infusion tube 200 is occluded on the downstream side 200B of the infusion tube 200 depending on whether or not degree ($\Delta$) of swelling (diameter expansion) of the outer diameter of the infusion tube 200 reaches the threshold value (whether or not the infusion tube 200 is in an occlusion state) by detecting and outputting the swelling thereof. The upstream occlusion sensor 52 and the downstream occlusion sensor 53 have the same configuration. As a case of occlusion in the infusion tube 200, high viscosity of drug to be delivered, high concentration of drug and the like are exemplified.

As illustrated in FIG. 3, on an inner surface side of the opening/closing cover 5, pressing members 452 and 453 are provided respectively at positions corresponding to the upstream occlusion sensor 52 and the downstream occlusion sensor 53. As a health care worker covers the infusion tube 200 with the opening/closing cover 5 as illustrated in FIG. 2 after setting the infusion tube 200 in the tube mounting portion 50 as illustrated in FIG. 3, the pressing member 452 and the pressing member 453 on the opening/closing cover 5 side can press portions of the infusion tube 200 respectively against the side of the upstream side occlusion sensor 52 and the downstream side occlusion sensor 53. Therefore, even though an infusion tube 200 of any size among multiple types of the infusion tubes 200 having diameters different from one another is mounted in the infusion pump 1, the upstream side occlusion sensor 52 and the downstream side occlusion sensor 53 can detect an occlusion state of the infusion tube 200 by causing the opening/closing cover 5 to be in the closed state.

Figure 4:
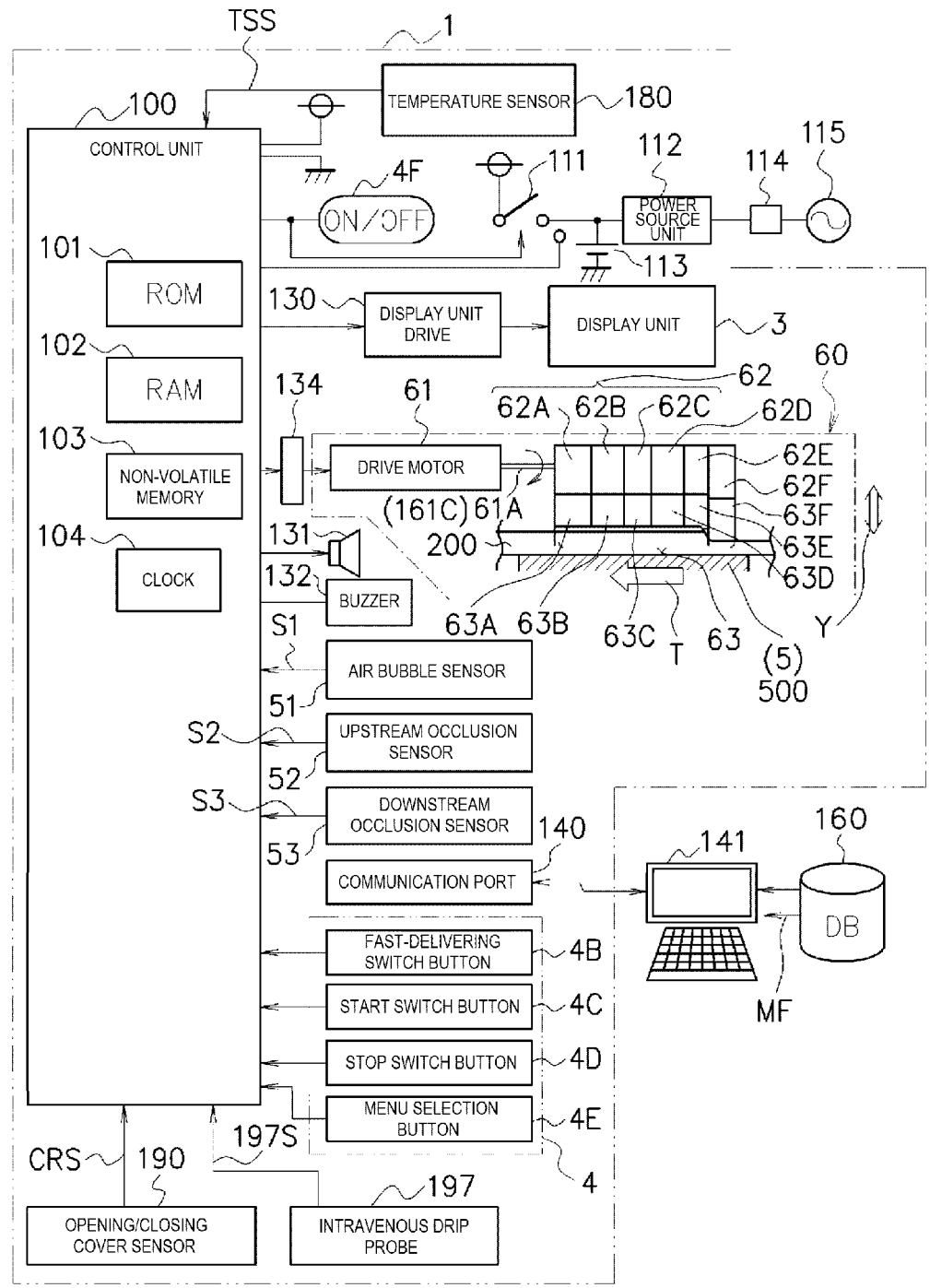
FIG. 4 is a diagram illustrating an example of an electrical configuration of the infusion pump.

As illustrated in FIG. 4, the infusion pump 1 has a control unit (a computer) 100 which judges and controls the entire operation. The control unit 100 is a one-chip microcomputer, for example, and includes a read-only memory (ROM) 101, a random access memory (RAM) 102, a non-volatile memory 103, and a clock 104. In the clock 104, the current time can be corrected through a prejudged operation. In addition, the current time can be acquired, an elapsed time of prejudged delivering can be measured, and a reference time for controlling a delivering rate can be measured, for example.

A temperature sensor 180, an opening/closing cover (opening/closing door) sensor 190, and an intravenous drip probe 197 are electrically connected to the control unit 100. The temperature sensor 180 measures a temperature of an environment where the infusion pump 1 is located, thereby sending a temperature measurement signal TSS. As the opening/closing cover 5 illustrated in FIG. 1 is in the open state, the opening/closing cover sensor 190 sends an opening/closing cover opening/closing signal CRS to the control unit 100. The intravenous drip probe 197 is arranged in the drug bag 170 illustrated in FIG. 2 and detects a falling state of droplets of drug, thereby sending a detection signal to the control unit 100.

The power switch button 4F and a switch 111 are connected to the control unit 100 illustrated in FIG. 4. The switch 111 performs switching between a power converter unit 112 and a rechargeable battery 113 such as a lithium-ion battery, for example, so as to supply a power source to the control unit 100 from either the power converter unit 112 or the rechargeable battery 113. The power converter unit 112 is connected to a commercial AC power source 115 through a power plug 114.

Returning back to FIG. 4, a display unit driver 130 drives the display unit 3 in response to a command of the control unit 100, thereby displaying information contents or a warning message exemplified in FIG. 2. The speaker 131 can notify a health care worker of various contents of warnings through audio in response to a command of the control unit 100. The buzzer 132 can notify a health care worker of various warnings through a sound in response to a command of the control unit 100. The speaker 131 is an example of warning means for issuing a warning to a health care worker through audio when the infusion tube 200 is set in the N-direction which is an erroneous direction (the reverse direction). The buzzer 132 is another example of warning means for issuing a warning to a health care worker through a sound when the infusion tube 200 is set in the N-direction which is an erroneous direction (the reverse direction).

In FIG. 4, the control unit 100 is supplied with an air bubble detection signal S1 from the air bubble sensor 51, an upstream occlusion signal S2 from the upstream occlusion sensor 52 indicating that the infusion tube 200 is occluded on the upstream side, and a downstream occlusion signal S3 from the downstream occlusion sensor 53 indicating that the infusion tube 200 is occluded on the downstream side. The upstream occlusion sensor 52 and the downstream occlusion sensor 53 can detect a state where an internal pressure of an infusion circuit exceeds a set pressure inside the infusion pump 1 so that drug cannot be delivered. The state where an internal pressure of the infusion circuit exceeds the set pressure inside the infusion pump 1 is caused when the infusion indwelling needle or the infusion tube 200 is blocked, when the infusion tube 200 is squashed or bent, when drug having high viscosity is used, and the like.

In FIG. 4, the control unit 100 can communicate bi-directionally with a computer 141 such as a desktop computer, for example, through a communication port 140. The computer 141 is connected to drug database (DB) 160. Drug information MF stored in the drug database 160 can be acquired by the control unit 100 through the computer 141 and can be stored in the non-volatile memory 103 of the control unit 100. The control unit 100 can display the drug information MF and the like on the display unit 3 illustrated in FIG. 2, for example, based on the stored the drug information MF.

As the drug information MF, the name of a manufacturer of drug, the name of drug, the upper and lower limits for a planned dosage quantity (mL) of drug, the upper and lower limits for a flow rate (mL/h), contraindicated information and the like are exemplified.

As the drive motor 61 and an output shaft 61A of the drive motor 61 in the liquid delivering drive unit 60 illustrated in FIG. 4 rotate, eccentric cams 62A to 62F provided in a cam structure body 62 which is pivotally supported by the output shaft 61A rotate, thereby causing a plurality of fingers 63A to 63F to sequentially move back and forth in the Y-direction in as many prejudged strokes (distance between the top dead center and the bottom dead center). A step motor is used as the drive motor 61. The cam structure body 62 has the plurality of cams, for example, the plurality of cams 62A to 62F. A finger structure body 63 has the plurality of fingers 63A to 63F respectively corresponding to the plurality of cams 62A to 62F. The plurality of cams 62A to 62F are arrayed so as to be respectively applied with phase differences. The cam structure body 62 is interlocked with the output shaft 61A.

As the output shaft 61A of the drive motor 61 rotates in response to a command of the control unit 100 illustrated in FIG. 4, the plurality of fingers 63A to 63F sequentially move back and forth in the Y-direction in as many prejudged strokes. Thus, the infusion tube 200 is pressed against the infusion tube pressing member 500 of the opening/closing cover 5 along the T-direction. Therefore, drug inside the infusion tube 200 can be delivered in the T-direction. In other words, the plurality of fingers 63A to 63F are individually driven, and the plurality of fingers 63A to 63F sequentially press an outer circumferential surface of the infusion tube 200 along the T-direction, thereby delivering drug inside the infusion tube 200. In this manner, in accordance with a sub-control unit 400 controlling peristaltic movements of the plurality of fingers 63A to 63F, the fingers 63A to 63F sequentially move back and forth as if waves ripple so as to move an occluded point of the infusion tube 200 in the T-direction, and the infusion tube 200 is squeezed. Thus, drug can be delivered in the T-direction.

Subsequently, with reference to FIG. 5, a description will be given regarding an example in which the drug 171 inside the infusion tube 200 is delivered by causing the finger structure body 63 of the liquid delivering drive unit 60 to press the infusion tube 200.

FIGS. 5(A) to 5(F) illustrate a so-called mid-press-type liquid delivering drive unit 60 which delivers the drug 171 by squeezing the infusion tube 200 in the T-direction so as to press the inside of the infusion tube 200. In other words, the liquid delivering drive unit 60 causes the fingers 63C, 63D, and 63E to sequentially press partway the infusion tube 200, excluding the fingers 63B and 63F which completely and closely press the infusion tube 200, thereby delivering the drug 171 inside the infusion tube 200. In this manner, the infusion tube 200 is not completely squashed by the finger structure body 63 of the mid-press-type liquid delivering drive unit 60. Therefore, it is possible to accurately deliver an amount of the necessary drug 171 to be delivered, by squashing a certain quantity of the infusion tube 200 within a range causing less deformation and fatigue in the infusion tube 200.

In FIG. 5(A), the infusion tube 200 is completely and closely pressed by the finger 63B, and the drug 171 flows into the infusion tube 200 in the T-direction. In FIG. 5(B), the drug 171 stops flowing, and the infusion tube 200 is shut down by the finger 63F. Thus, a certain amount of the drug 171 can be secured between the fingers 63B and 63F inside the infusion tube 200.

In FIG. 5(C), the finger 63B is released from completely pressing the infusion tube 200, and the finger 63E presses partway the infusion tube 200. Moreover, in FIG. 5(D), the fingers 63D and 63C sequentially press partway the infusion tube 200, thereby discharging the drug 171 in the T-direction.

In FIG. 5(E), the finger 63B presses the infusion tube 200 again, and the drug 171 stops to be discharged in the T-direction (the same state as the state in FIG. 5(A)). Thereafter, the procedure returns to the initial state in FIG. 5(A). The drug 171 can be delivered in the T-direction by repeating the procedure of pressing the infusion tube 200 described above.

Subsequently, with reference to FIG. 6, a description will be given regarding a structural example of the drive motor 61, and a rotational direction detection device 700 for detecting a rotational direction of an output shaft 161C of the drive motor 61. FIG. 6 illustrates the structural example of the drive motor 61, and the rotational direction detection device 700 for detecting the rotational direction of the output shaft 161C of the drive motor 61. FIG. 7 illustrates an example of detection information 780 regarding the rotational direction obtained from an encoder plate 701.

Figure 6A:
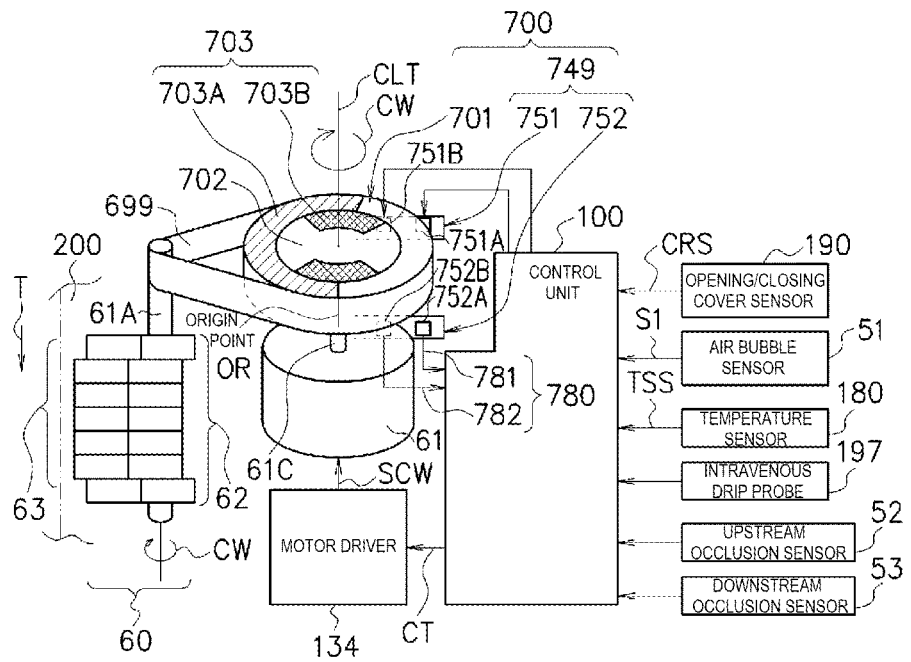
FIGS. 6A and 6B are diagrams illustrating a structural example of a drive motor, and a rotational direction detection device for detecting a rotational direction of an output shaft of the drive motor.
Figure 6B:
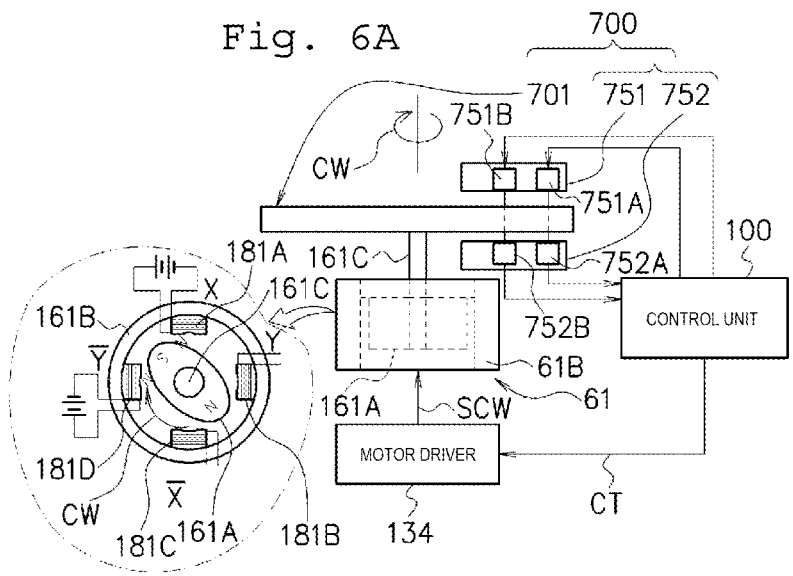

FIG. 6(A) illustrates the drive motor 61, the rotational direction detection device 700 for detecting the rotational direction of the output shaft 161C of the drive motor 61, and the liquid delivering drive unit 60. FIG. 6(B) illustrates the structural example of the drive motor 61, and the rotational direction detection device 700 for detecting the rotational direction of the output shaft 161C of the drive motor 61.

As illustrated in FIG. 6(A), the control unit 100 is electrically connected to the drive motor 61 through a motor driver 134. As the control unit 100 issues a command CT to the motor driver 134, the motor driver 134 can cause the drive motor 61 to rotate forward. A step motor (a stepping motor) is preferably used as the drive motor 61. As exemplified in FIG. 6(B), the drive motor 61 is a 2-phase 4-pole-type step motor or the like, for example. However, the step motor may be structured to be a three-phase step motor, for example.

As illustrated in FIG. 6(B), in a case of the 2-phase 4-pole-type step motor, the drive motor 61 has a magnet rotor 161A and an electromagnet stator 161B. The magnet rotor 161A is a permanent magnet having the N-pole and the S-pole and is rotatable in the stator 161B. The magnet rotor 161A is fixed to the output shaft 161C illustrated in FIG. 6. The stator 161B has four excitation coils which are arranged every 90 degrees in the clockwise direction, for example. In the four excitation magnet coils, a coil 181A is an X-terminal, a coil 181B is a Y-terminal, a coil 181C is an X-bar terminal, and a coil 181D is a Y-bar terminal.

The magnet rotor 61A is set to rotate in the forward rotation direction CW when a 2-phase excitation pulse-like input current waveform SCW for forward rotation illustrated in FIG. 10(A) is applied to the coils 181A, 181B, 181C, and 181D of the drive motor 61 illustrated in FIG. 6(B) from the motor driver 134 in order, in response to the command CT of the control unit 100 illustrated in FIG. 4. In this manner, an angle of the magnet rotor 161A in the rotational direction can be accurately controlled by employing the step motor as the drive motor 61. In a stationary state, since the magnet rotor 161A is fixed due to magnetism, a force of the magnet rotor 161A to be stationary is great, thereby being suitable for stopping at a certain angle.

As illustrated in FIGS. 6(A) and 6(B), the rotational direction detection device 700 is configured to have the encoder plate 701 and an optical coupler 749. The disk-type encoder plate 701 is fixed to the output shaft 161C. The encoder plate 701 includes a light transmitting pattern portion 702 which has a preset shape and allows light to pass therethrough, and a light blocking pattern portion 703 which allows no light to pass therethrough. The light blocking pattern portion 703 has an outer circumferential region 703A which is at a position on an outer circumferential side about a central axis CLT, and an inner circumferential region 703B which is at a position on an inner circumferential side about the central axis CLT. The outer circumferential region 703A is a one-fan-shaped portion when the encoder plate 701 rotates in the forward rotation direction CW having the central axis CLT as the center. In contrast, the inner circumferential region 703B is two fan-shaped portions when the encoder plate 701 rotates in the forward rotation direction CW having the central axis CLT as the center.

As illustrated in FIG. 6(A), the output shaft 161C and the output shaft 61A are individually formed in the actual drive motor 61. The encoder plate 701 is fixed onto the output shaft 161C side, and the output shaft 61A is interlocked to the cam structure body 62 of the liquid delivering drive unit 60. An outer circumferential surface of the encoder plate 701 is interlocked to the output shaft 61A on the cam structure body 62 side by using a belt 699.

As illustrated in FIGS. 6(A) and 6(B), the optical coupler 749 is arranged in the vicinity of the encoder plate 701. The optical coupler 749 has a light emitting unit 751 and a light receiving unit 752. The light emitting unit 751 is arranged on one surface side of the encoder plate 701 and has two light emitting diodes 751A and 751B. The light receiving unit 752 is arranged on the other surface side of the encoder plate 701 and has two light receiving diodes 752A and 752B. Accordingly, as the control unit 100 causes the light emitting diodes 751A and 751B of the light emitting unit 751 to emit light, the light receiving diodes 752A and 752B of the light receiving unit 752 respectively at the corresponding positions can receive light.

As the motor driver 134 applies the 2-phase excitation pulse-like input current waveform SCW for forward rotation to the drive motor 61 in response to the command CT of the control unit 100 illustrated in FIG. 6(A), the magnet rotor 161A and the output shaft 161C of the drive motor 61 continuously rotate in the forward rotation direction CW. Accordingly, since the encoder plate 701 rotates in the forward rotation direction CW, light emitted from the light emitting diodes 751A and 751B passes through the light transmitting pattern portion 702 and is blocked by the light blocking pattern portion 703. In this example, if light of the light emitting diodes 751A and 751B is blocked by the light blocking pattern portion 703, the light receiving diodes 752A and 752B apply a signal High (H) to the control unit 100. If light of the light emitting diodes 751A and 751B is transmitted through the transmitting pattern portion 702, the light receiving diodes 752A and 752B apply a signal Low (L) to the control unit 100.

Accordingly, as illustrated in FIG. 7, the control unit 100 illustrated in FIG. 6(A) obtains information of the rotational speed together with the detection information 780 from the encoder plate 701 regarding the rotational direction (whether the forward rotation or the reverse rotation). The detection information 780 regarding the rotational direction indicates positional information which relates to the rotational direction of the encoder plate 701, that is, positional information of the magnet rotor 161A of the drive motor 61. FIG. 7 exemplifies the detection information 780 regarding the rotational direction, and the detection information 780 regarding the rotational direction includes a first output waveform signal 781 illustrated in FIG. 7(A), and a second output waveform signal 782 illustrated in FIG. 7(B). The first output waveform signal 781 is the first output waveform signal, and the second output waveform signal 782 is the second output waveform signal. The period of the cycle of the second output waveform signal 782 is double compared to the period of the cycle of the first output waveform signal 781. Additionally, FIG. 7 illustrates an origin point OR of rotation, and a position (0), a position (1), a position (2), a position (3) a position (OA), a position (OB), and the position (OC) of the rotational direction. Here, a falling position of the second output waveform signal 782 is set as the origin point OR of rotation.

Each pulse cycle of the first output waveform signal 781 and each pulse cycle of the second output waveform signal 782 which is illustrated in FIG. 7(B) correspond to the rotational speed of the magnet rotor 161A of the drive motor 61. The rotational speed of the magnet rotor 161A of the drive motor 61 corresponds to an operational speed of each finger of the finger structure body 63. The operational speed of the fingers is substantially proportional to a flow rate of drug inside the infusion tube 200. Accordingly, the control unit 100 can control the flow rate of drug on account of each pulse cycle (a pulse rate) of the first output waveform signal 781 and each pulse cycle (a pulse rate) of the second output waveform signal 782 which is illustrated in FIG. 7(B). Since the pulse rate increases if a pulse width is narrowed, and the pulse rate decreases if the pulse width is widened, the control unit 100 controls the pulse rate, that is, the flow rate of drug by adjusting the pulse width.

FIG. 8 illustrates a judgment table 798 indicating judgment examples of the magnet rotor 161A and the output shaft 161C of the drive motor 61 of FIG. 6(A) in the forward rotation direction CW or the reverse rotation direction CCW based on the detection information 780 regarding the rotational direction illustrated in FIG. 7. In respect to the detection information 780 regarding the rotational direction illustrated in FIG. 7, the control unit 100 in FIG. 6(A) compares current encoder information IF1 and immediately preceding (immediate past) encoder information IF0 immediately preceding the current encoder information IF1 which are indicated in the judgment table 798 of FIG. 8, thereby being able not only to judge whether the magnet rotor 161A and the output shaft 161C rotate in the forward rotation direction CW, rotate in the reverse rotation direction CCW, or in a state other than thereof but also to judge whether or not the rotational speed is normal as well based on the information of the rotational speed.

The judgment table 798 illustrated in FIG. 8 indicates judgment criteria for the control unit 100. The judgment table 798 is previously stored in the ROM 101 illustrated in FIG. 4, for example.

With reference to FIG. 8, the examples of the judgment contents of the judgment table 798 will be sequentially described. The judgment table 798 in FIG. 8 indicates the current encoder information IF1 and the immediately preceding encoder information IF0.

In the judgment table 798 of FIG. 8, "L:L" denotes a case where "the first output waveform signal 781 is at Low level:the second output waveform signal 782 is at Low level".

"L:H" denotes a case where "the first output waveform signal 781 is at the Low level:the second output waveform signal 782 is at High level".

"H:L" denotes a case where "the first output waveform signal 781 is at the High level:the second output waveform signal 782 is at the Low level". Then, "H:H" denotes a case where "the first output waveform signal 781 is at the High level:the second output waveform signal 782 is at the High level".

Moreover, the judgment table 798 in FIG. 8 indicates item sections (1-1) to (1-4) in the lateral direction and indicates item sections (2-1) to (2-4) in the vertical direction.

Subsequently, an operational example of the infusion pump 1 will be described.

When a health care worker presses the power switch 4F illustrated in FIG. 4 so as to cause infusion pump 1 to be switched on, the control unit 100 illustrated in FIG. 6(A) issues the command CT to the motor driver 134, thereby operating the drive motor 61. When the drive motor 61 operates, the output shaft 61A of the cam structure body 62 continuously rotates in the forward rotation direction CW via the belt 699 in accordance with the continuous rotations of the output shaft 161C and the encoder plate 701 of the drive motor 61 in the forward rotation direction CW, illustrated in FIG. 6(A). Accordingly, the cam structure body 62 presses each finger of the finger structure body 63, and thus, each finger sequentially presses the outer circumferential surface of the infusion tube 200 along the T-direction, thereby delivering drug inside the infusion tube 200.

In this manner, as the output shaft 161C and the encoder plate 701 of the drive motor 61 continuously rotates in the forward rotation direction CW, the control unit 100 obtains the detection information 780 regarding the rotational direction from the encoder plate 701. The detection information 780 regarding the rotational direction is the positional information of the encoder plate 701, that is, the positional information of the magnet rotor 161A of the drive motor 61.

The detection information 780 regarding the rotational direction illustrated in FIG. 7 is characterized by including the first output waveform signal 781 and the second output waveform signal 782.

Meanwhile, since an occlusion pressure is mitigated when the control unit 100 receives a downstream occlusion signal S3 from the downstream occlusion sensor 53 indicating that a downstream side of the infusion tube 200 is in an occlusion state from the downstream occlusion sensor 53, the drive motor 61 is caused to stop continuously rotating in the forward rotation direction CW. Thereafter, the drive motor 61 is caused to reversely rotate while judging whether or not the drive motor 61 is driven in the reverse rotation.

A plurality of prejudged conditions for stopping the reverse rotation are set as described in the following 1) to 4), for example. However, the conditions are examples, and the embodiment is not limited thereto.

1) An output by the Hall element drops to the extent of 80% with respect to a value corresponding to an occlusion state.

2) "The quantity of reverse rotation" has a prejudged number of steps.

3) The integrated dosage becomes less than the integrated dosage when liquid starts to be delivered.

4) The integrated dosage becomes zero.

The control unit 100 illustrated in FIG. 6 can judge a positional change, that is, whether the magnet rotor 161A and the output shaft 161C of the drive motor 61, and the output shaft 61A of the cam structure body 62 illustrated in FIG. 6(A) are in the forward rotation state or the reverse rotation state, according to the judgment table 798 illustrated in FIG. 8.

With reference to FIGS. 6(A), 7, and 8, the judgment examples of the positional change of the magnet rotor 161A and the output shaft 161C of the drive motor 61 will be described.

In the judgment table 798 of FIG. 8, since the current encoder information IF1 is "L:L" in the item section (1-1), and the immediately preceding encoder information IF0 is "L:L" in the item section (2-1), with reference to FIG. 7, the control unit 100 judges that there is "no positional change" of the magnet rotor 161A of the drive motor 61.

In the judgment table 798 of FIG. 8, since the current encoder information IF1 is "L:H" in the item section (1-2), and the immediately preceding encoder information IF0 is "L:L" in the item section (2-1), with reference to FIG. 7, the control unit 100 judges that the magnet rotor 161A of the drive motor 61 is in "the forward rotation:the position (2)".

In the judgment table 798 of FIG. 8, since the current encoder information IF1 is "H:L" in the item section (1-3), and the immediately preceding encoder information IF0 is "L: L" in the item section (2-1), with reference to FIG. 7, the control unit 100 judges that the magnet rotor 161A of the drive motor 61 is at "the position OB in the forward rotation:the positions OA and OC in the reverse rotation".

In the judgment table 798 of FIG. 8, since the current encoder information IF1 is "H:H" in the item section (1-4), and the immediately preceding encoder information IF0 is "L:L" in the item section (2-1), with reference to FIG. 7, the control unit 100 judges that the magnet rotor 161A of the drive motor 61 is in "the rotation state:the position is unidentified".

Subsequently, in the judgment table 798 of FIG. 8, since the current encoder information IF1 is "L:L" in the item section (1-1), and the immediately preceding encoder information IF0 is "L:H" in the item section (2-2), with reference to FIG. 7, the control unit 100 judges that the magnet rotor 161A of the drive motor 61 is in "the reverse state (the reverse rotation):the position (2)".

In the judgment table 798 of FIG. 8, since the current encoder information IF1 is "L:H" in the item section (1-2), and the immediately preceding encoder information IF0 is "L:H" in the item section (2-2), with reference to FIG. 7, the control unit 100 judges that there is "no positional change" of the magnet rotor 161A of the drive motor 61.

In the judgment table 798 of FIG. 8, since the current encoder information IF1 is "H:L" in the item section (1-3), and the immediately preceding encoder information IF0 is "L:H" in the item section (2-2), with reference to FIG. 7, the control unit 100 judges that the magnet rotor 161A of the drive motor 61 is in "the rotation:the position is unidentified".

In the judgment table 798 of FIG. 8, since the current encoder information IF1 is "H:H" in the item section (1-4), and the immediately preceding encoder information IF0 is "L:H" in the item section (2-2), with reference to FIG. 7, the control unit 100 judges that the magnet rotor 161A of the drive motor 61 is in "the forward rotation:the position (3)".

Subsequently, in the judgment table 798 of FIG. 8, since the current encoder information IF1 is "L:L" in the item section (1-1), and the immediately preceding encoder information IF0 is "H:L" in the item section (2-3), with reference to FIG. 7, the control unit 100 judges that the magnet rotor 161A of the drive motor 61 is at "the positions OA and OC in the forward rotation:the position OB in the reverse rotation".

In the judgment table 798 of FIG. 8, since the current encoder information IF1 is "L:H" in the item section (1-2), and the immediately preceding encoder information IF0 is "H:L" in the item section (2-3), with reference to FIG. 7, the control unit 100 judges that the magnet rotor 161A of the drive motor 61 is in "the rotation:the position is unidentified".

In the judgment table 798 of FIG. 8, since the current encoder information IF1 is "H:L" in the item section (1-3), and the immediately preceding encoder information IF0 is "H:L" in the item section (2-3), with reference to FIG. 7, the control unit 100 judges that there is "no positional change" of the magnet rotor 161A of the drive motor 61.

In the judgment table 798 of FIG. 8, since the current encoder information IF1 is "H:H" in the item section (1-4), and the immediately preceding encoder information IF0 is "H:L" in the item section (2-3), with reference to FIG. 7, the control unit 100 judges that the magnet rotor 161A of the drive motor 61 is in "the reverse state (the reverse rotation): the position (1)".

In the judgment table 798 of FIG. 8, since the current encoder information IF1 is "L:L" in the item section (1-1), and the immediately preceding encoder information IF0 is "H:H" in the item section (2-4), with reference to FIG. 7, the control unit 100 judges that the magnet rotor 161A of the drive motor 61 is in "the rotation:the position is unidentified".

In the judgment table 798 of FIG. 8, since the current encoder information IF1 is "L:H" in the item section (1-2), and the immediately preceding encoder information IF0 is "H: H" in the item section (2-4), with reference to FIG. 7, the control unit 100 judges that the magnet rotor 161A of the drive motor 61 is in "the reverse state (the reverse rotation): the position (3)".

In the judgment table 798 of FIG. 8, since the current encoder information IF1 is "H:L" in the item section (1-3), and the immediately preceding encoder information IF0 is "H:H" in the item section (2-4), with reference to FIG. 7, the control unit 100 judges that the magnet rotor 161A of the drive motor 61 is in "the forward rotation:the position (1)".

In the judgment table 798 of FIG. 8, since the current encoder information IF1 is "H:H" in the item section (1-4), and the immediately preceding encoder information IF0 is "H:H" in the item section (2-4), with reference to FIG. 7, the control unit 100 judges that there is "no positional change" of the magnet rotor 161A of the drive motor 61.

As described above, the control unit 100 in FIG. 6(A) can judge whether the magnet rotor 161A and the output shaft 161C of the drive motor 61, and the output shaft 61A of the cam structure body 62 are in the forward rotation state at the faster rotational speed, that is, the 3×-speed, in the reverse rotation state, or in a state other than thereof based on the combination of the current encoder information IF1 and the immediately preceding encoder information IF0 illustrated in FIG. 8, by obtaining the first output waveform signal 781 and the second output waveform signal 782 illustrated in FIG. 7. As the control unit 100 judges the positional change, the forward rotation and the reverse rotation of the rotor of the drive motor can be detected. Thus, it is possible to safely deliver drug to a patient. In order to prevent the downstream side from being temporarily (instantaneously) stopped in delivering drug, the magnet rotor 161A and the output shaft 161C of the drive motor 61, and the output shaft 61A of the cam structure body 62 are controlled to be at 3× speed during a period until the state reaches that illustrated in FIG. 5(B) via the states illustrated in FIGS. 5(E) to 5(A).

In a case of a so-called full-press-type infusion pump in which all of the fingers completely and closely press the infusion tube 200 in order, the speed is controlled to be faster than the 1× speed while the finger on the farthest downstream side (corresponding to the finger 63A) completely releases the infusion tube 200 from the closely pressed state and the finger on the farthest upstream side (corresponding to the finger 63F) completely and closely presses the infusion tube 200.

As necessary, when the magnet rotor 161A and the output shaft 161C of the drive motor 61, and the output shaft 61A of the cam structure body 62 are in the reverse rotation instead of the forward rotation, the control unit 100 can display "the drive motor is in the reverse rotation" on the display unit 3, can notify a health care worker of "the reverse rotation of the drive motor" through audio by using the speaker 131 illustrated in FIG. 4, or can issue an alarm through a sound by using the buzzer 132.

For example, when the magnet rotor 161A and the output shaft 161C of the drive motor 61, and the output shaft 61A of the cam structure body 62 are in the reverse rotation, the control unit 100 can promptly stop the operation of the drive motor 61.

The infusion pump 1 according to the embodiment of the present invention includes the drive motor, the liquid delivering drive unit that delivers drug inside the infusion tube by pressing the infusion tube on account of the rotor of the drive motor in forward rotation, the rotational direction detection device that generates detection information regarding a rotational direction for judging whether the rotor of the drive motor is in the forward rotation or the reverse rotation, and the control unit that judges whether the rotor of the drive motor is in the forward rotation or the reverse rotation based on the detection information regarding the rotational direction obtained from the rotational direction detection device. Accordingly, the control unit can judge whether the rotor of the drive motor is in the forward rotation or the reverse rotation based on the detection information regarding the rotational direction obtained from the rotational direction detection device. Therefore, it is possible to detect the forward rotation and the reverse rotation of the rotor of the drive motor so as to be able to safely deliver drug to a patient.

The rotational direction detection device includes the encoder plate which is fixed to the rotor of the drive motor, and the optical coupler which obtains the first output waveform signal and the second output waveform signal different from the first output waveform signal by irradiating the encoder plate with light so as to send the first output waveform signal and the second output waveform signal to the control unit as the detection information regarding the rotational direction. Accordingly, it is simply performed that the optical coupler optically generates the first output waveform signal and the second output waveform signal so as to send to the control unit as the detection information regarding the rotational direction of the rotor. And thus, it is possible to simplify the structure thereof.

The first output waveform signal is the output waveform signal generated from the inner circumferential region of the light-shield pattern 703B and the second output waveform signal is the output waveform signal generated from the outer circumferential region of the light shield pattern 703A. The control unit judges whether the rotor is in the forward rotation or the reverse rotation by comparing the first output waveform signal and the second output waveform signal. Accordingly, since the control unit has only to compare the first output waveform signal and the second output waveform signal, it is possible to accurately judge whether the rotor is in the forward rotation or the reverse rotation.

The liquid delivering drive unit includes the plurality of cams which rotate on account of the forward rotation of the drive motor, and the plurality of fingers which deliver the drug inside the infusion tube while sequentially pressing the infusion tube in the longitudinal direction on account of the plurality of cams in rotation. Accordingly, the plurality of fingers can reliably deliver drug inside the infusion tube to a patient side by causing the plurality of cams to rotate forward.

The display unit displaying information and the operation panel portion having the operation buttons are arranged in the upper portion of the main body of the infusion pump, and the infusion tube is arranged in a region of the lower portion of the main body of the infusion pump. Accordingly, a health care worker can perform delivering of drug by using the infusion pump while confirming the information on the display unit in the upper portion of the main body. Then, the health care worker can operate the operation button of the operation panel portion while confirming the information on the display unit in the upper portion of the main body.

The present invention is not limited to the above-described embodiment, and thus, various changes and modifications can be made without departing from the scope of the Claims.

Figure 5:
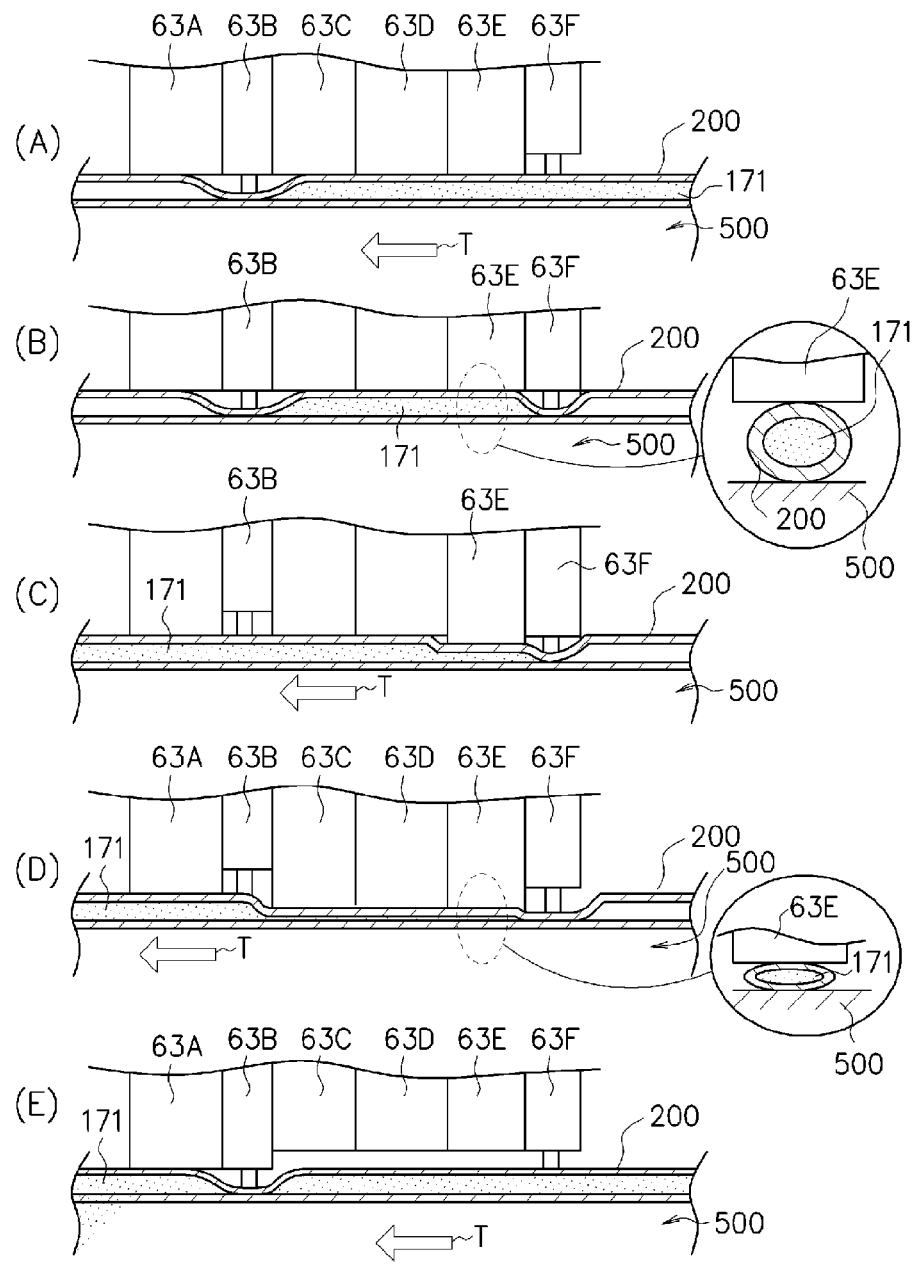
FIG. 5 is a diagram illustrating a mid-press-type liquid delivering drive unit which delivers drug inside the infusion tube by squeezing and pressing the infusion tube.

In FIG. 5, as the liquid delivering drive unit 60, the embodiment of the infusion pump of the present invention exemplifies a mid-press-type liquid delivering drive unit which delivers the drug 171 inside the infusion tube 200 by pressing the infusion tube 200 without completely squashing. However, without being limited thereto, as the liquid delivering drive unit 60, a full-press-type liquid delivering drive unit may be employed which delivers the drug 171 inside the infusion tube 200 by completely squashing the infusion tube 200.

Each configuration in the above-described embodiment can be partially omitted and can be arbitrarily combined so as to be different from above.

REFERENCE SIGNS LIST

1 . . . infusion pump,
3 . . . display unit,
50 . . . tube mounting portion,
60 . . . liquid delivering drive unit,
61 . . . drive motor,
100 . . . control unit,
101 . . . ROM,
161A . . . magnet roller (rotor),
171 . . . drug,
200 . . . infusion tube,
700 . . . rotational direction detection device,
749 . . . optical coupler,
780 . . . detection information regarding rotational direction,
781 . . . output waveform signal at 1× speed (first output waveform signal),
782 . . . output waveform signal at 3× speed (second output waveform signal), and
798 . . . judgment table

The invention claimed is:

1. An infusion pump for delivering a drug to a patient by causing a distal opening portion of an endovascular indwelling catheter or an indwelling needle, which communicates with an infusion tube, to indwell inside a vein or an intestinal tract of the patient, the infusion pump comprising:
- a drive motor;
- a liquid delivering drive unit that delivers the drug inside the infusion tube by pressing the infusion tube based on a rotor of the drive motor rotating in forward rotation;
- a rotational direction detection device including an encoder plate having a light-blocking inner circumferential region that produces a first number of pulses per cycle when the encoder plate rotates in a forward rotation direction and a different light-blocking outer circumferential region that produces a second number of pulses per cycle other than the first number of pulses per cycle when the encoder plate rotates in the forward rotation direction, wherein the rotational direction detection device generates detection information regarding a rotational direction for judging whether the rotor of the drive motor is in the forward rotation or reverse rotation, wherein the encoder plate is fixed to the rotor of the drive motor and an optical coupler which obtains a first output waveform signal by the light-blocking inner circumferential region and a second output waveform signal by the light-blocking outer circumferential region that is different from the first output waveform signal by irradiating the encoder plate with light; and
- a control unit, wherein the control unit judges, based on a judgment table, which indicates judgment examples of a forward rotation direction or a reverse rotation direction, and a combination of a current encoder information and an immediately preceding encoder information, whether the rotor of the drive motor is in the forward rotation or the reverse rotation based on the detection information regarding the rotational direction obtained from the rotational direction detection device, while the rotor is moving, wherein each of the current encoder information and the immediately preceding encoder information is the first output waveform signal and the second output waveform signal, and wherein the control unit also judges whether a rotational speed of the rotor is normal based on the first number of pulses per cycle associated with the first output waveform signal and the second number of pulses per cycle associated with the second output waveform signal.

2. The infusion pump according to claim 1, wherein the liquid delivering drive unit includes a plurality of cams which rotate based on the forward rotation of the drive motor, and a plurality of fingers which deliver the drug inside the infusion tube while sequentially pressing the infusion tube in a longitudinal direction based on the plurality of cams in rotation.

3. The infusion pump according to claim 1, wherein a display unit displaying information and an operation panel portion having an operation button are arranged in an upper portion of a main body of the infusion pump, and the infusion tube is arranged in a region of a lower portion of the main body of the infusion pump.

4. The infusion pump according to claim 1, further comprising:
- a display unit, arranged in an upper portion of a main body of the infusion pump, the display unit configured to display information associated with the infusion pump; and
- an operation panel portion, having an operation button.

5. The infusion pump according to claim 1, wherein the light-blocking inner circumferential region is corradial with an inner circumferential light transmitting pattern portion, and wherein the light-blocking outer circumferential region is corradial with an outer circumferential light transmitting pattern portion.

6. The infusion pump according to claim 5, wherein the optical coupler comprises a light emitting unit disposed on a first side of the encoder plate and a light receiving unit disposed on an opposite second side of the encoder plate.

7. The infusion pump according to claim 6, wherein light emitted by the light emitting unit passes through the encoder plate to the light receiving unit at the inner circumferential light transmitting pattern portion and at the outer circumferential light transmitting pattern portion of the encoder plate.

8. An infusion pump for delivering a drug to a patient by causing a distal opening portion of an endovascular indwelling catheter or an indwelling needle, which communicates with an infusion tube, to indwell inside a vein or an intestinal tract of the patient, the infusion pump comprising:
- a drive motor;
- a liquid delivering drive unit that delivers the drug inside the infusion tube by pressing the infusion tube based on a rotor of the drive motor in forward rotation;
- a rotational direction detection device including an encoder plate having a light-blocking inner circumferential region that produces a first number of pulses per cycle when the encoder plate rotates in a forward rotation direction and a different light-blocking outer circumferential region that produces a second number of pulses per cycle different from the first number of pulses per cycle when the encoder plate rotates in the forward rotation direction, wherein the rotational direction detection device generates detection information regarding a rotational direction for judging whether the rotor of the drive motor is in the forward rotation or reverse rotation;
- an optical coupler which obtains a first output waveform signal by the light-blocking inner circumferential region and a second output waveform signal by the light-blocking outer circumferential region that is different from the first output waveform signal by irradiating the encoder plate with light;
- a downstream occlusion sensor that detects whether the infusion tube is occluded; and
- a control unit, wherein the control unit judges, based on a judgment table, which indicates judgment examples of a forward rotation direction or a reverse rotation direction, and a combination of a current encoder information and an immediately preceding encoder information, whether the rotor of the drive motor is in the forward rotation or the reverse rotation based on the detection information regarding the rotational direction obtained from the rotational direction detection device, wherein, while causing the rotational direction detection device to detect that the rotor of the drive motor is in the forward rotation and if an occlusion state is detected by the downstream occlusion sensor when delivering liquid in the forward rotation, the control unit stops the forward rotation, and wherein, while causing the rotational direction detection device to detect that the rotor of the drive motor is in the reverse rotation, the control unit controls the drive motor to be driven in the reverse rotation until fulfilling a prejudged condition wherein each of the current encoder information and the immediately preceding encoder information is only the first output waveform signal and the second output waveform signal, and wherein the control unit also judges whether a rotational speed of the rotor is normal based on the first number of pulses per cycle associated with the first output waveform signal and the second number of pulses per cycle associated with the second output waveform signal.

9. The infusion pump according to claim 8, wherein the liquid delivering drive unit further comprises:
    a plurality of cams which rotate based on the forward rotation of the drive motor; and
    a plurality of fingers, coupled to the plurality of cams, which deliver the drug inside the infusion tube while sequentially pressing the infusion tube in a longitudinal direction based on the rotation of the plurality of cams.

10. The infusion pump according to claim 9, further comprising:
    a display unit, arranged in an upper portion of a main body of the infusion pump, the display unit configured to display information associated with the infusion pump; and
    an operation panel portion, having an operation button.

11. The infusion pump according to claim 8, further comprising:
    a display unit, arranged in an upper portion of a main body of the infusion pump, the display unit configured to display information associated with the infusion pump; and
    an operation panel portion, having an operation button.

12. The infusion pump according to claim 8, wherein the light-blocking inner circumferential region is corradial with an inner circumferential light transmitting pattern portion, and wherein the light-blocking outer circumferential region is corradial with an outer circumferential light transmitting pattern portion.

13. The infusion pump according to claim 12, wherein the optical coupler comprises a light emitting unit disposed on a first side of the encoder plate and a light receiving unit disposed on an opposite second side of the encoder plate.

14. The infusion pump according to claim 13, wherein light emitted by the light emitting unit passes through the encoder plate to the light receiving unit at the inner circumferential light transmitting pattern portion and at the outer circumferential light transmitting pattern portion of the encoder plate.

15. A control method of an infusion pump including a control unit for delivering a drug to a patient by causing a distal opening portion of an endovascular indwelling catheter or an indwelling needle, which communicates with an infusion tube, to indwell inside a vein or an intestinal tract of the patient, the control method comprising:
    driving a drive motor coupled by a rotor to a liquid delivering drive unit;
    pressing the infusion tube by the liquid delivering drive unit longitudinally in a first or second direction based either on a forward rotation or a reverse rotation of the rotor of the motor and delivering the drug to a patient;
    generating detection information regarding a rotational direction of the rotor by a rotational direction detection device including an encoder plate having a light-blocking inner circumferential region that produces a first number of pulses per cycle when the encoder plate rotates in a forward rotation direction and a different light-blocking outer circumferential region that produces a second number of pulses per cycle other than the first number of pulses per cycle when the encoder plate rotates in the forward rotation direction, and an optical coupler irradiating the encoder plate wherein the optical coupler obtaining a first output waveform signal from the light-blocking inner circumferential region or a second output waveform signal from the light-blocking outer circumferential region that is different from the first output waveform signal based on the irradiation, and sending either the first output waveform signal or the second output waveform signal to the control unit;
    determining whether the drive motor is in the forward rotation or the reverse rotation and judging whether a rotational speed of the rotor is normal;
    detecting whether the infusion tube is occluded by a downstream occlusion sensor;
    wherein when an occlusion state of the infusion tube is detected by the downstream occlusion sensor while delivering the drug in the forward rotation, stopping, by the control unit, the forward rotation;
    after stopping the forward rotation, controlling, by the control unit, the drive motor to be driven in a reverse rotation until fulfilling a prejudged condition; and
    judging, by the control unit, based on a judgment table indicating judgment examples of a forward rotation direction or a reverse rotation direction and a combination of a current encoder information and an immediately preceding encoder information, whether the rotor of the drive motor is in the forward rotation or the reverse rotation, based on the detection information regarding the rotational direction obtained from the rotational direction detection device, wherein each of the current encoder information and the immediately preceding encoder information is the first output waveform signal and the second output waveform signal, and whether the rotational speed of the rotor is normal based on the first number of pulses per cycle associated with the first output waveform signal and the second number of pulses per cycle associated with the second output waveform signal.

16. The method according to claim 15, further comprising:
    judging, via the control unit, whether the rotor is in the forward rotation or the reverse rotation by comparing a shape of the first output waveform signal and the second output waveform signal over time.

17. The method according to claim 15, further comprising:
    displaying, via a display unit arranged in an upper portion of a main body of the infusion pump, information associated with the infusion pump.

18. The method according to claim 17, further comprising:
    receiving, at an operation panel portion having an operation button, input from a user.

19. The method according to claim 18, further comprising:
    rotating a plurality of cams based on the forward rotation of the drive motor; and
    sequentially pressing, via a plurality of fingers coupled to the plurality of cams, the infusion tube in a longitudinal direction based on the rotation of the plurality of cams.

20. The method according to claim 15, wherein the light-blocking inner circumferential region is corradial with an inner circumferential light transmitting pattern portion, wherein the light-blocking outer circumferential region is corradial with an outer circumferential light transmitting pattern portion, wherein the optical coupler comprises a light emitting unit disposed on a first side of the encoder plate and a light receiving unit disposed on an opposite second side of the encoder plate, and wherein light emitted by the light emitting unit passes through the encoder plate to the light receiving unit at the inner circumferential light transmitting pattern portion and at the outer circumferential light transmitting pattern portion of the encoder plate.

\* \* \* \* \*